United States Patent
Bayer et al.

(10) Patent No.: US 8,173,196 B2
(45) Date of Patent: May 8, 2012

(54) METHOD OF COATING A STENT WITH A POLYSACCHARIDE LAYER AND ASSOCIATED STENTS

(75) Inventors: Gerd Bayer, Erlangen (DE); Markus Nagel, Forchheim (DE); Alexander Borck, Aurachtal (DE)

(73) Assignee: Biotronik Mess-und Therapiegeraete GmbH & Co., Ingenieurbuero Berlin (DE)

( * ) Notice: Subject to any disclaimer, the term of this patent is extended or adjusted under 35 U.S.C. 154(b) by 1176 days.

(21) Appl. No.: 11/531,512

(22) Filed: Sep. 13, 2006

(65) Prior Publication Data

US 2007/0026038 A1    Feb. 1, 2007

Related U.S. Application Data

(62) Division of application No. 10/444,827, filed on May 23, 2003, now abandoned.

(30) Foreign Application Priority Data

May 24, 2002    (DE) .................... 102 23 310

(51) Int. Cl.
    *A61L 33/00*    (2006.01)
(52) U.S. Cl. ......... 427/2.1; 424/486; 424/426; 514/291; 428/420; 427/2.3; 427/2.31; 427/385.5; 427/388.4; 427/407.1; 427/2.24; 623/1.15; 623/11; 623/1; 623/900; 623/901
(58) Field of Classification Search ............. 623/1.15, 623/11, 1, 900, 901; 428/420; 514/291; 424/426, 486, 427, 429
See application file for complete search history.

(56) References Cited

U.S. PATENT DOCUMENTS

| 4,957,744 A | 9/1990 | della Valle et al. |
| 4,979,959 A | 12/1990 | Guire |
| 5,263,992 A | 11/1993 | Guire |
| 5,356,433 A | 10/1994 | Rowland et al. |
| 5,562,922 A * | 10/1996 | Lambert ................. 424/486 |
| 5,718,726 A | 2/1998 | Amon et al. |
| 6,042,876 A | 3/2000 | Deem |
| 6,120,536 A | 9/2000 | Ding et al. |
| 6,193,752 B1 | 2/2001 | Hildebrandt |
| 6,361,819 B1 | 3/2002 | Tedeschi et al. |
| 6,673,453 B2 * | 1/2004 | Beavers et al. ................. 428/420 |
| 2002/0035395 A1 * | 3/2002 | Sugimoto ................. 623/1.15 |
| 2002/0123505 A1 * | 9/2002 | Mollison et al. ............. 514/291 |
| 2004/0249438 A1 | 12/2004 | Lefranc et al. |

FOREIGN PATENT DOCUMENTS

| WO | 00/56377 A1 | 9/2000 |
| WO | 01/41827 A1 | 6/2001 |
| WO | 02/18003 A1 | 3/2002 |
| WO | 02/39948 A2 | 5/2002 |
| WO | 03/011355 A1 | 2/2003 |

OTHER PUBLICATIONS

Hildebrandt, et al., "Prevention of surface encrustation of urological implants by coating with inhibitors," Biomaterials, Elsevier Science Ltd., p. 503-507, (Oct. 9, 2001).

* cited by examiner

*Primary Examiner* — Dah-Wei Yuan
*Assistant Examiner* — Andrew Bowman
(74) *Attorney, Agent, or Firm* — Hahn Loeser & Parks LLP; John J. Cunniff

(57) ABSTRACT

The invention concerns methods of coating stents and stents produced in accordance therewith. The object of the invention is to provide methods of coating stents with a polysaccharide layer which has improved adhesion capacity on the substrate surface of the implant, and to afford correspondingly functionalized stents. That is achieved inter alia by covalent bonding of a non-crosslinked hyaluronic acid to a substrate surface of the stent with the formation of hyaluronic acid layer and crosslinking of the hyaluronic acid layer.

20 Claims, No Drawings

METHOD OF COATING A STENT WITH A POLYSACCHARIDE LAYER AND ASSOCIATED STENTS

This application is a divisional application of application Ser. No. 10/444,827, filed May 23, 2003, which claims priority from German Application No. 102 23 310.1, filed May 24, 2002.

The invention concerns methods of coating stents, in particular cardiovascular implants, with a polysaccharide layer or polysaccharide derivative layer, and stents produced in accordance with such methods.

BACKGROUND OF THE ART

In regard to the background of the invention it is to be stressed that polysaccharides are known to be biocompatible. Typical representatives in this connection are heparin, chitosan, alginate or hyaluronic acid. The latter have proven on the one hand to be highly body-compatible while on the other hand coatings of hyaluronic acid are hydrophilic and consequently the devices provided therewith can be well implanted.

Implants coated with polysaccharides in general and hyaluronic acid in particular and methods of coating them with hyaluronic acid are known from the state of the art in many different forms. Thus, U.S. Pat. No. 6,042,876, to Deem (Mar. 28, 2000), discloses a guide wire for implantation purposes, which is coated with such a polysaccharide such as hyaluronic acid or chondroitin sulfate.

Della Valle, in U.S. Pat. No. 4,957,744 (Sep. 18, 1990), teaches the crosslinking of esters of hyaluronic acid which are used for the most widely varying medical and cosmetic articles, as well as pharmaceutical compositions. The crosslinked esters result from the esterification of polyvalent alcohols with two or more carboxy groups of hyaluronic acid. Such crosslinked esters can be used in particular in the field of bioresorbable plastic materials for medical and surgical articles.

Finally, PCT publication WO 8802623 A1, by Guire at Bio-Metric Systems, Inc., relates to biomaterials with a biocompatible surface, wherein among a large number of starting materials and binding mechanisms there is disclosed inter alia the use of hyaluronic acid for the production of a biocompatible contact lens. This publication is related to U.S. Pat. Nos. 4,979,959 and 5,263,992.

Insofar as the above-mentioned publications concern coating methods for medical equipment and in particular stents, they suffer from the disadvantage that the polysaccharide layers produced do not achieve adequate levels of adhesive strength on the substrate surface.

Accordingly the object of the present invention is to provide a method of coating stents with a polysaccharide layer which enjoys improved adhesion on the substrate surface of the implant, and to afford correspondingly functionalized stents.

SUMMARY OF THE INVENTION

That object is attained by the alternative methods having the features of the appended claims as well as the associated stent. Specifically, the object is attained by the following characterizing method steps:

covalent bonding of a non-crosslinked hyaluronic acid to the substrate surface of the stent forming the polysaccharide layer, and crosslinking of the hyaluronic acid layer (variant I).

In an alternative configuration of the method of the invention, instead of crosslinking of the applied non-crosslinked hyaluronic acid layer, a further layer of a crosslinked hyaluronic acid is applied to the first non-crosslinked hyaluronic acid layer (variant II).

In accordance with a third variant (III) according to the invention the method is carried out as follows:

covalent bonding of a non-crosslinked hyaluronic acid to a substrate surface of the stent forming a first hyaluronic acid layer, covalent bonding of a second non-crosslinked layer of hyaluronic acid, and crosslinking of the second hyaluronic acid layer.

A fourth variant (IV) provides that the method steps are to be carried out as follows:

bonding of a bonding agent layer to a substrate surface of the stent, covalent bonding of a non-crosslinked hyaluronic acid to the bonding agent layer forming a hyaluronic acid layer, and crosslinking of the hyaluronic acid layer.

Finally in accordance with a fifth variant (V) the coating operation is effected in the following manner:

bonding a bonding agent layer to a substrate surface of the stent, covalent bonding of a non-crosslinked first layer of chitosan to the bonding agent layer forming a chitosan layer, and applying a second layer of crosslinked or non-crosslinked hyaluronic acid.

Basic variants I and V of the methods according to the invention, by virtue of covalent bonding of the non-crosslinked polysaccharide, provide for a significant increase in the adhesive capability of the polysaccharide layer, which can be demonstrated by experiment. In that respect the further layer can be applied in the form of a non-crosslinked polysaccharide and can then be crosslinked or it can be applied directly as a crosslinked polysaccharide.

Further advantages in particular of variant II lie in the primary application of a uniform polysaccharide layer and coupling thereto of a secondary, preferably thicker layer which, in contrast to other hydrogel films of comparable thickness, has a low swelling capacity. By virtue of their physical and chemical properties polysaccharide layers such as hydrogel films or polymer matrices are suitable for embedding active substances in order to enhance the biocompatible action by means of local active substance liberation or locally to achieve a pharmacological action. In comparison with conventional hydrogel films or polymer matrices, polysaccharide layers of glycosaminoglycans, in particular, hyaluronic acid, additionally have their own pharmacological action.

An especially suitable polysaccharide for use in the method according to the invention is hyaluronic acid, which has already been referred to above, and which can be applied to the most widely varying substrate surfaces of implants. Alloplastic vessel wall supports—referred to as "stents"—are usually coated with amorphous silicon carbide (a-SiC:H) which involves a particularly intimate and adhesively strong bond to hyaluronic acid.

Finally, functional coating can be achieved by the alternate application of a respective plurality of layers of non-crosslinked and crosslinked polysaccharides.

Further features, details and advantages of the invention will be apparent from the embodiments hereinafter.

DETAILED DESCRIPTION OF A PREFERRED EMBODIMENT

The method according to the invention is described by reference to the coating of a substrate surface of amorphous silicon carbide which is applied for example to a stent with a basic structure consisting of a tantalum alloy. The essential features of activation of the silicon carbide substrate surface can be found in that respect from the present applicants' German patent application DE 195 33 682 A1, which discloses the application and immobilization of heparin on a silicon carbide coating.

I. Bonding of Polysaccharides

Example 1

Bonding by Way of a Benzophenone Derivative

In accordance therewith the substrate surface was flushed with water and incubated in a $20 \times 10^{-6}$-molar Fmoc-p-Bz-Phe-OH-solution in N,N'-dimethylformamide (DMF). The Fmoc-p-Bz-Phe-OH-solution, which is effective as a photoactive spacer substance, can be obtained as a commercial product "Fmoc-p-Bz-Phe-OH", product number B 2220 from Bachem Biochemica GmbH, of Heidelberg, Germany. Reduction of the benzophenone was initiated by irradiation with UV light. After the UV irradiation operation, the reaction solution was poured off and the substrate surface rinsed a plurality of times with distilled water.

The next step involves cleavage of the Fmoc protective group with 25% piperidine solution in DMF. Bonding of the hyaluronic acid takes place at the amino group which is now exposed and reactive. For that purpose, non-crosslinked hyaluronic acid was firstly covalently bound to the substrate surface treated in that way. The polysaccharide layer formed in that fashion can then be crosslinked.

As an alternative to the above-described photochemical reaction, it is possible for polysaccharides, and, in particular, hyaluronic acid, to be covalently bound in a wet-chemical process to silanized benzophenones, epoxysilanes and aminosilanes as spacer substances to the substrate surface, in particular to the silicon carbide substrate surface.

Example 2

Bonding by Way of Silanized Benzophenone Derivative

Wet-chemical covalent bonding of a silanized benzophenone, in particular 4-(3'-chlorodimethylsilyl)propyloxybenzophenone, was effected by a wet-chemical procedure in an organic solvent such as toluene at ambient temperature overnight in the presence of $Et_3N$ as a catalyst. After the incubation time, the substrates were rinsed in chloroform and then in methanol. Thereafter the layer system of substrate spacer was wetted with a 0.1%-2% aqueous hyaluronic acid solution and then dried. Covalent bonding of the hyaluronic acid to the benzophenone present was effected under the action of UV radiation at a wavelength of 340 nm which initiates the reduction of the benzophenone. Alternatively the photochemical reaction can also be implemented in aqueous hyaluronic acid solution. That photochemical reaction resulted in covalent bonding between the benzophenone and a C—H-group of the polymer chain, in particular of the hyaluronic acid. That polysaccharide layer, which was covalently bound to the substrate surface, was then crosslinked.

Example 3

Bonding by Way of Epoxysilanes

For wet-chemical coating of silicon carbide substrates with epoxysilanes, the substrates were firstly cleaned and then dried for an hour at a temperature of 75° C. Silanization of the warm substrate was effected with (3-(2,3-epoxypropoxy)-propyl)-trimethoxysilane with immersion in organic solvent. The silanized substrates were then dried and washed in the organic solvent. Subsequent covalent bonding of the hyaluronic acid was effected in an aqueous solvent overnight with agitation at ambient temperature. Alternatively bonding of hyaluronic acid can be effected by incubation in a 0.25% hyaluronic acid solution in a 0.1 m HCl at 65° C. for 1 h. Chitosan can be bound by incubation in a 0.2% chitosan solution in a 1-2% acetic acid solution at 65° C. for 1 h. The stents were then rinsed with deionized water and thereafter dried. The polysaccharide layer, which is covalently bound to the substrate surface, was then crosslinked.

Example 4

Bonding of Chitosan

A good adhesive effect can be achieved by a covalently bound chitosan layer (monolayer). The glycosaminoglycan chitosan (Mw: 100,000 to 1,000,000 Daltons) was covalently bonded by means of a spacer in a chemical multi-stage reaction to an amorphous silicon carbide layer (a-SiC:H) which covers the basic body of the stent In the first step of the coating process the spacer—the photoactive benzophenone component Fmoc-p-Bz-Phe-OH (N-(9-Fmoc)-l-(4-benzoyl)-phenylalanine; 2 ml; 10 mmol/l; available from Bachem)—was covalently bonded to the silicon carbide by photochemical reaction in the solvent N,N'-dimethylformamide (DMF). After rinsing with DMF, cleavage was effected in respect of the Fmoc protective group of the spacer with a 20% piperidine solution in DMF. The amino group of the spacer was then free.

The stent was then incubated in a 0.2% solution of chitosan in 1% acetic acid and N-(3-dimethylaminopropyl)-N'-ethyl-carbodiimide hydrochloride (50 mg/ml) for at least 12 hours in ice-cold water. Covalent coupling of the chitosan was effected by linkage of a peptide bond between the activated carboxylic acid of the spacer and the amino group of the chitosan or the formation of an ester bond between the activated carboxylic acid of the spacer and the hydroxyl group of the chitosan. After the end of the reaction the sample was repeatedly rinsed with deionized water and then dried.

Example 5

Bonding to Plasma-Deposited Polymer

An example of use for the application of a bonding agent layer is described in greater detail hereinafter. A polymer layer which is a few nanometers thick was applied to the cleaned substrate surface. The polymer layer served as a bonding agent and had functional groups at the surface, which are suitable for subsequent covalent bonding of a polysaccharide layer. Such a bonding agent layer can be produced by plasma polymerization of N-heptylamine and acetaldehyde.

The plasma polymerization operation was effected with a 40 kHz plasma installation of Piko type from Diener electronics. As an alternative to the above-mentioned precursor it is possible to use acetaldehyde, amyl alcohol, allylamine, acetoacetic acid ester or acrylic acid. The plasma-polymerized layers exhibited good wetting with hyaluronic acid solutions by virtue of their hydrophilic nature. In addition a thin layer of hyaluronic acid or other polysaccharides can be coupled to the functional surfaces by means of glutaraldehyde, epichlorhydrin or carbodiimides.

The container was flushed with oxygen for the definitive removal of residual gas, in which case it is continuously evacuated. A flushing gas flow of about 40 cm$^3$/min was set. The sample space was flushed for 10 minutes and the plasma was ignited in the presence of a Teflon block for the surface activation procedure. The power of the reactor was about 200 W and an oxygen flow of about 40 cm$^3$/min was maintained during the surface treatment. Activation and simultaneous plasma purification lasted for 5-10 min.

After activation and cleaning were effected, the power was reduced to 80 W and the precursor is introduced into the container. The polymerization period was 5 min with the aerometer open. After it was been switched off, further surface activation was effected with oxygen, but then the power was only 80 W with a duration of about 30 sec. This short surface activation operation resulted in a still further improvement in wettability of the surfaces.

Taking the deposited bonding agent layer comprising the N-heptylamine plasma polymer, the hyaluronic acid was then covalently bonded by means of a water-soluble carbodiimide to the substrate-bonding agent layer complex. Covalent bonding of the hyaluronic acid to the acetaldehyde plasma polymer was effected directly by means of a diimidazole or with bonding of a polyethylene imine intermediate layer which is applied by means of reductive amination. Covalent bonding of the hyaluronic acid to that substrate-bonding agent complex was effected by means of a water-soluble carbodiimide. The polysaccharide layer which is covalently bonded to the bonding agent layer was then crosslinked.

Example 6

Bonding by Way of Derivatized Polyhydroxybutyric Acid

As an alternative to the method of plasma polymerization, the substrate surface was functionalized by derivatized polyhydroxybutyric acid, which exhibits an experimentally demonstrated good layer adhesion to silicon carbide and metals. Functionalization of the polyhydroxybutyric acid was effected by amination. Covalent bonding of the hyaluronic acid to the amino group of the functionalized polyhydroxybutyric acid (bonding agent layer) was effected by means of a water-soluble carbodiimide, with the formation of a peptide bond.

Example 7

Bonding of Chitosan by Way of an Aminosilane

A monolayer of chitosan was produced in the following manner. The pre-cleaned stent was dried at 75° C. for 30 minutes in a drying oven. Then, the stent, while still warm, was incubated for 10 minutes in a silane solution of 3 ml of water-free toluene, 20 μl of 3-[2-(2-aminoethylamino)-ethylamino]-propyl-trimethoxysilane and 70 μl of Et$_3$N at ambient temperature with repeated slight agitation. The stents were then dried at 75° C. for 1 hour. Thereafter the stent was rinsed with toluene or chloroform and dried again. The next step was covalent coupling of adipinic acid by way of a solution of 10 mg/ml of adipinic acid in water for the production of functional carbonyl functions, to the surface of the implant. The adipinic acid had been previously activated in THF or DMF with a carbodiimide or diimidazole. After rinsing in deionized water and drying, the operation of bonding chitosan took place. For that purpose the implant was incubated in a 0.2% solution of chitosan in a 1-2% acetic acid solution at ambient temperature for 1-4 hours. That was followed by rinsing with deionized water and drying.

II. Crosslinking and Coating Methods

Crosslinking and coating methods of hyaluronic acid on implant surfaces will now be described in greater detail. The described methods are suitable in this respect for:
  crosslinking a non-crosslinked polysaccharide layer which is covalently bonded to the substrate,
  covalently bonding a non-crosslinked polysaccharide to a crosslinked or non-crosslinked polysaccharide layer, or
  covalently bonding a crosslinked polysaccharide to a crosslinked or non-crosslinked polysaccharide layer.

Example 8

Crosslinking with Glutaraldehyde

The crosslinking of hyaluronic acid with glutaraldehyde can be implemented. The implant was coated with a 0.1-2% hyaluronic acid solution and then subjected to the action of a crosslinker solution for several hours. The crosslinker solution comprised 240 ml of acetone, 80 ml of glutaraldehyde in 25% solution in water and 1.6 ml of HCl 3 M. Thereafter the crosslinker solution was replaced by a fresh solution and incubation was again effected at ambient temperature for several hours. The hyaluronic acid crosslinked by means of glutaraldehyde was washed several times in distilled water. The sample was incubated in a 0.5-3% solution of sodium cyanoborohydride for one hour at ambient temperature. The fixer solution was removed and the procedure then involved a plurality of washing steps in doubly distilled water and isotonic saline solution.

Crosslinking of the hyaluronic acid with bifunctional aldehydes and formaldehyde was effected in a method similarly to crosslinking of the hyaluronic acid with glutaraldehyde.

Example 9

Crosslinking with Epichlorhydrin 0.38 g of hyaluronic acid was dissolved in 90 ml of water for the crosslinking of hyaluronic acid by epichlorhydrin. 10 g of NaOH and 6.8 ml of aqueous ammonia solution (25%) were added to the solution. The temperature of the reaction solution was set at 20° C. After that temperature was reached, 19.6 ml of epichlorhydrin was added thereto. The solution was stirred at 20° C. for 24 hours. The crosslinked hyaluronic acid was then dialyzed in relation to doubly distilled water. The dialysis hoses used have an exclusion limit of 120,000 DA.

Example 10

Crosslinking with Divinyl Sulfone

For the crosslinking of hyaluronic acid by divinyl sulfone, 2 g of hyaluronic acid was dissolved in 50 ml of 0.1 m aqueous NaOH solution, giving a 2% solution. The solution was put on ice. When temperature equalization was effected, 2 ml of divinyl sulfone was added. The resulting two-phase mixture was agitated for 15 minutes on ice. After 5 minutes, only one phase was still to be observed. The implants were immersed in that solution and then dried.

Example 11

Crosslinking with Ethylene Glycol Diglycidylether

For the crosslinking of hyaluronic acid with ethylene glycol diglycidylether, a 0.1-2% hyaluronic acid solution in a 0.9% isotonic saline solution was produced. The reaction was conducted at 25° C. As the crosslinking agent, up to 10 molar percent of ethylene glycol diglycidylether was added, with respect to the repetition unit of the hyaluronic acid.

Example 12

Crosslinking with Diimidazole

It is also possible to implement crosslinking and covalent bonding of the hyaluronic acid to layer systems comprising amorphous silicon carbide spacer and an amorphous silicon carbide-spacer-polysaccharide monolayer with diimidazole. The implant with bound spacer or with a polysaccharide layer was immersed in a diimidazole-bearing acetone solution. The substrate-spacer complex or the polysaccharide layer was activated for at least 30 minutes in the diimidazole-bearing acetone solution and then immersed in an aqueous hyaluronic acid solution or sprayed with a hyaluronic acid solution. For the spray coating operation, the stent was sprayed for 0.5-1 sec at a pressure in respect of the carrier air of 2-4 bars. Between the spraying steps, the stent was dried for 15-30 sec with a supply of warm air. Repeating the steps makes it possible to produce a desired layer structure on the stent. In order to achieve layer growth, that process was repeated a plurality of times.

Example 13

Crosslinking with Acid Dichlorides or Phosphorus Oxychloride

The crosslinking of the OH- and NHR-groups of polysaccharides was effected by means of acid dichlorides or phosphorus oxychloride with the formation of ester or amide groups and with the liberation of HCl in an organic solvent.

III. Derivatization of the Polysaccharide Layer

Derivatization of the coated hyaluronic acid hydrogel on the implant can also be implemented.

Example 14

Sulfatization

By virtue of polymer-analogous transformation of hyaluronic acid, for example, by means of an $SO_3$*pyridine complex, enzymatic decomposition of hyaluronic acid in vivo was delayed or hyaluronic acid was stabilized in the body, as the following example of use shows.

Hyaluronic acid was suspended in dry pyridine in a nitrogen atmosphere in a thermostatizable double-wall reactor with a reflux condenser and an agitator. A sulfur trioxide-pyridine-complex was added to that suspension and heated to the desired reaction temperature. After 3 hours, the reaction was terminated and the suspension, when cooled to ambient temperature, was poured into five times the amount of methanol. The precipitated polymer was filtered off, dissolved in water and dialyzed in relation to de-ionized water. As the product was partly in the form of pyridinium salt and the polymer chains were intermolecularly esterified with each other, the pH-value of the polymer solution after dialysis was adjusted to 11 by the addition of 0.1 N soda lye. Dialysis and titration were repeated three times. At a pH-value of 7.3 the polymer was freeze-dried.

A variation in the degree of sulfatization in this polymer-analogous transformation procedure is possible by virtue of the amount of added sulfatization reagent $SO_3$* pyridine, the reaction time and the reaction temperature.

IV. Embedding Drugs

Active substance loading with suitable drugs was generally effected after crosslinking and fixing of the polysaccharide layer in the swollen condition. Alternatively the active substance can be furnished by means of a spraying or immersion process prior to the coating step or during coating with the polysaccharide. Active substance embedding was generally effected by way of diffusion processes.

Example 15

Embedding Cyclosporin

The active substance was embedded by way of an immersion process in a hyaluronic acid layer as can be obtained in accordance with one of the preceding examples. For that purpose, the implant was immersed in a solution of 15 mg of cyclosporin per ml of a paritetic ethanol-water mixture. The ratio of 1:1 of ethanol to water has proven to be surprisingly effective for implementation of the diffusion process. Other ratios, especially those with an elevated ethanol content, slow down the embedding effect. Depending on the respective layer thickness and degree of crosslinking of the polysaccharide layer the implant remained in the solution for at least one hour. The implant was then removed and dried. With a coating amount of 0.5 mg of hyaluronic acid, the amount of cyclosporin which can be incorporated in that way was at least 0.2 mg.

What is claimed is:

1. A method of coating a surface of a stent with a polysaccharide layer the method comprising the steps of:
    providing the stent with a surface prepared for covalent bonding of a polysaccharide thereto;
    bonding a non-crosslinked hyaluronic acid covalently to the prepared surface, thereby providing a first non-crosslinked hyaluronic acid layer;
    covalent bonding of a crosslinked layer of hyaluronic acid to the first non-crosslinked hyaluronic acid layer; wherein an active substance is present in at least one of the polysaccharide layers.

2. A method of coating a surface of a stent with a polysaccharide layer, the method comprising the steps of:
    providing a stent with a surface prepared for the bonding of polysaccharide thereto by bonding a bonding agent layer to the substrate surface;
    covalent bonding of a non-crosslinked first layer of chitosan to the bonding agent layer forming a chitosan layer;
    bonding a layer of crosslinked hyaluronic acid covalently to the non-crosslinked chitosan; wherein an active substance is provided in at least one of the polysaccharide layers.

3. A method according to claim 2, wherein:
    the active substance is provided by means of a spraying or immersion process prior to the step of bonding a layer of crosslinked hyaluronic acid covalently to the chitosan.

4. A method according to claim 2, wherein:
the active substance is embedded after crosslinking and fixing of the polysaccharide layers in the swollen condition.

5. The method according claim 4, wherein:
the active substance is Cyclosporin.

6. The method according claim 2, wherein:
the active substance is Cyclosporin.

7. The method according claim 2, wherein the active substance is embedded by means of a spraying or immersion process during coating with the polysaccharide.

8. The method according claim 7, wherein:
the active substance is Cyclosporin.

9. A method according to claim 2, wherein:
the secondary layer is thicker than the first polysaccharide layer.

10. A method according to claim 9, wherein:
the active substance is provided by means of a spraying or immersion process prior to the step of bonding a layer of crosslinked hyaluronic acid covalently to the chitosan.

11. The method according claim 10, wherein:
the active substance is Cyclosporin.

12. The method according claim 9, wherein:
the active substance is Cyclosporin.

13. The method according claim 9, wherein the active substance is embedded by means of a spraying or immersion process during coating with the polysaccharide.

14. The method according claim 13, wherein:
the active substance is Cyclosporin.

15. A method of coating a surface of a stent with a polysaccharide layer, the method comprising the steps of:
providing a stent with a surface prepared for the bonding of polysaccharide thereto by bonding a bonding agent layer to the substrate surface;
covalent bonding of a non-crosslinked first layer of chitosan to the bonding agent layer forming a chitosan layer;
bonding a layer of non-crosslinked hyaluronic acid covalently to the chitosan;
embedding an active substance in the polysaccharide layers.

16. A method according to claim 15 wherein:
the secondary layer is thicker than the first polysaccharide layer.

17. A method according to claim 15, wherein:
the active substance is embedded after crosslinking and fixing of the polysaccharide layers in the swollen condition.

18. A method according to claim 15, wherein:
the active substance is provided by means of a spraying or immersion process prior to the step of bonding a layer of crosslinked hyaluronic acid covalently to the chitosan.

19. The method according claim 15, wherein the active substance is embedded by means of a spraying or immersion process during coating with the polysaccharide.

20. The method according claim 15, wherein:
the active substance is Cyclosporin.

\* \* \* \* \*